US00PP30018P3

(12) United States Plant Patent
Breneliere

(10) Patent No.: US PP30,018 P3
(45) Date of Patent: Dec. 25, 2018

(54) ***ELAEAGNUS* 'ABRELA'**

(50) Latin Name: *Elaeagnus ebbingei*
Varietal Denomination: Abrela

(71) Applicant: Albert Breneliere, Machecoul (FR)

(72) Inventor: Albert Breneliere, Machecoul (FR)

( * ) Notice: Subject to any disclaimer, the term of this patent is extended or adjusted under 35 U.S.C. 154(b) by 0 days.

(21) Appl. No.: 15/530,930

(22) Filed: Mar. 24, 2017

(65) Prior Publication Data

US 2018/0279528 P1 Sep. 27, 2018

(51) Int. Cl.
*A01H 5/00* (2018.01)

(52) U.S. Cl.
USPC ..... Plt./226

(58) Field of Classification Search
USPC ..... Plt./226
See application file for complete search history.

(56) References Cited

PUBLICATIONS http://www.sapho.fr/gb/trees-and-shrubs/228-elaeagnus-x-ebbingei-maryline-abrela-.html Jul. 3, 2015.*
http://www.newplantsandflowers.com/bright-leaves-make-maryline-stand-out-over-a-long-distance/ Aug. 17, 2015.*
PLUTO Plant Variety Database Jan. 20, 2018. p. 1.*

* cited by examiner

*Primary Examiner* — Annette H Para
(74) *Attorney, Agent, or Firm* — Cassandra Bright

(57) ABSTRACT

A new and distinct *Elaeagnus* cultivar named 'Abrela' is disclosed, characterized by a distinctive yellow foliage with a thin green margin and new growth with pink stems. Plants are compact growing and suitable for hedging. The new cultivar is a *Elaeagnus*, suitable for ornamental garden purposes.

2 Drawing Sheets

Latin name of the genus and species: *Elaeagnus ebbingei.*
Variety denomination: 'Abrela'.

BACKGROUND OF THE INVENTION

The new cultivar is a product of chance discovery by the inventor. This new variety, hereinafter referred to as 'Abrela', was discovered as a naturally occurring, whole plant mutation by the inventor, Albert Breneliere. The interesting new mutation was discovered in a commercial nursery in Machecoul, France among plants of the unpatented *Elaeagnus ebbingei* 'Macrophylla' during Summer of 2000.

After identifying the new variety as a potentially interesting selection, the inventor first organized propagation of 'Abrela' by hardwood cuttings at a commercial nursery in Machecoul, France in the Fall of 2000. Rooted cuttings of the new variety were first planted during Spring of 2001. The inventor continued controlled testing and propagation, assessing stability of the unique characteristics of this variety. Significant effort was made by the inventor to develop the most stable clone of the variety, over several years. At least three generations have been reproduced and have shown that the unique features of this cultivar are stable and reproduced true to type.

SUMMARY OF THE INVENTION

The cultivar 'Abrela' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Abrela' These characteristics in combination distinguish 'Abrela' as a new and distinct *Elaeagnus* cultivar:

1. Unique yellow foliage with a green edge.
2. Pink stems on new growth.
3. Compact growth.
4. Suitability as a hedge.

COMPARISON TO PARENT VARIETY

'Abrela' is similar in most horticultural characteristics to the parent variety.

Plants of the new cultivar 'Abrela', however, have mainly yellow foliage with a green margin, foliage of the parent variety is solid green.

COMMERCIAL COMPARISON

'Abrela' is similar in most horticultural characteristics to the unpatented commercial variety *Elaeagnus ebbingei* 'Limelight'. Plants of the new cultivar 'Abrela' however have significantly more yellow on the leaf blade than this comparator. Additionally, the new variety has brighter pink new stems.
Gilt edge, maculata, Frederici.

BRIEF DESCRIPTION OF THE PHOTOGRAPHS

Figure 1:
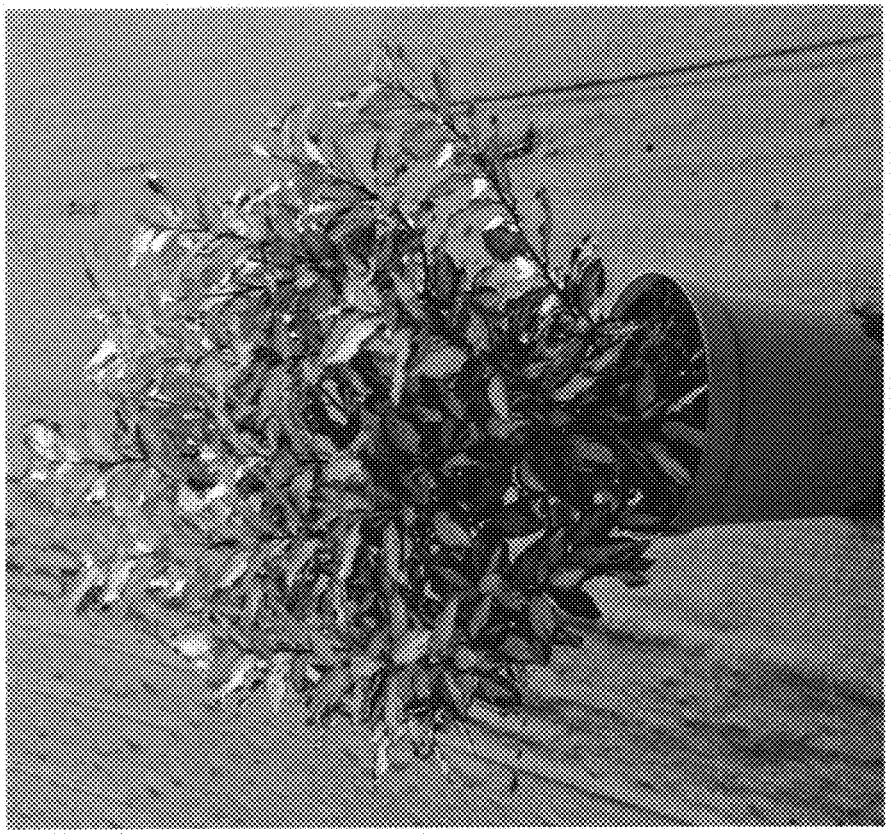

The accompanying photograph in FIG. 1 illustrates in full color a typical plant of 'Abrela' grown outdoors in Machecoul, France. The plant is approximately 1 year old, and is shown in a 3 liter container.

Figure 2:
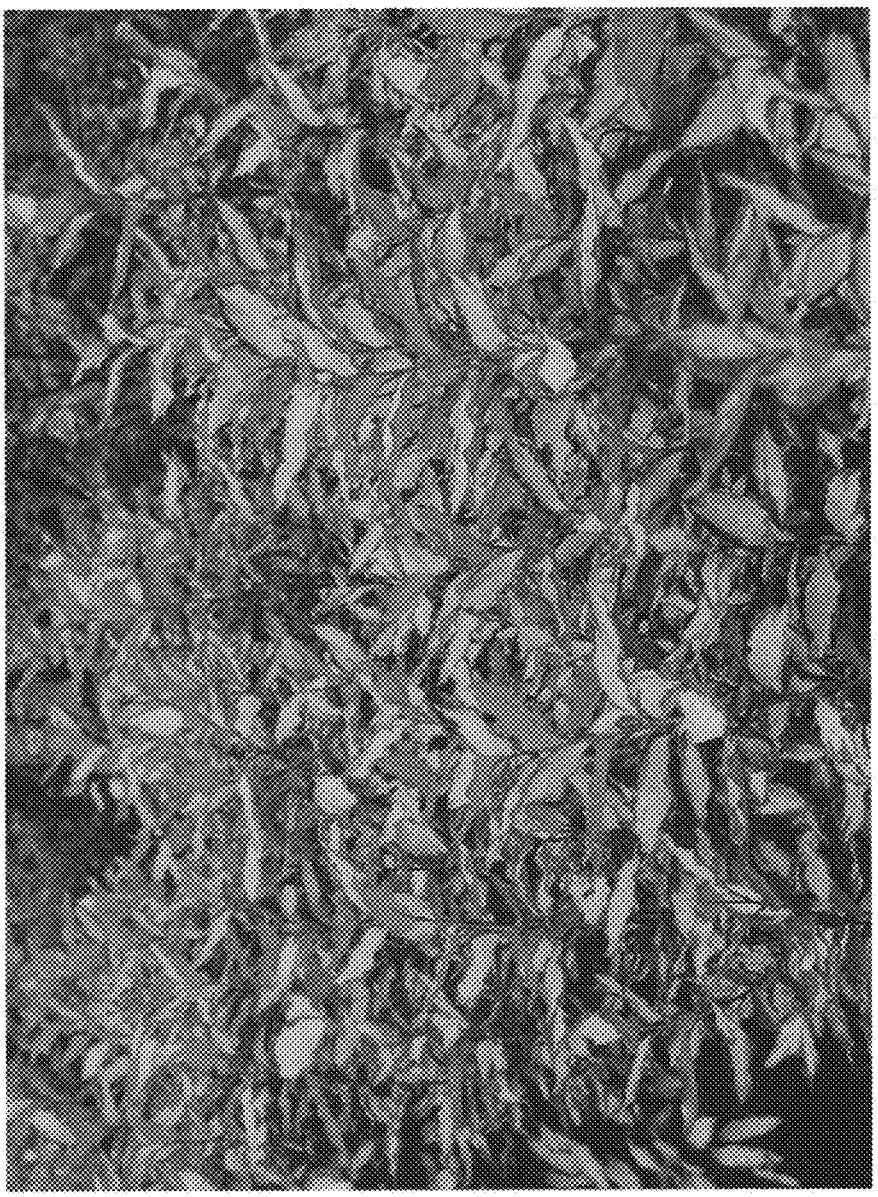

FIG. 2 illustrates a close up of foliage and new growth, including the distinctive pink stems.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Abrela' plants grown outdoors in Machecoul, France. Plants are approximately 2 years old, in a 2 gallon nursery container. Measurements and numerical values represent averages of typical plant types.

Botanical classification: *Elaeagnus ebbingei* 'Abrela'.

PROPAGATION

Time and method of propagation: Typically hardwood cuttings are taken in October/November, with rooted plantlet developed by April the following Spring.

Root description: Fibrous, very well branched. Colored near RHS Brown 199B, 199C.

PLANT

Growth habit: Orbicular, upright evergreen shrub.

Height: Approximately 200 to 250 cm. after 2 years.

Plant spread: Approximately 200 to 250 cm.

Typical growth rate: Moderate.

Branching characteristics: Moderate to dense branches. No single central stem. Approximately 15 to 20 main lateral branches, each of these with Lateral stems are held at an angle of approximately 45 degree from the center of the plant.

Length of lateral branches: Average range 50 to 180 cm.

Diameter of lateral branches: Approximately 0.9 cm.

Lateral branch shape in cross section: Generally round.

Lateral branch strength: Flexible, not easily broken.

Lateral branch color:

*New growth*.—Near Greyed-Red 180D.

*Mid-season*.—Near Greyed-Red 180A.

*Mature*.—Near RHS Greyed-Purple 183A.

Lateral branch texture: Glabrous.

Internode length: Average range 2.5 to 7.5 cm.

Lenticels present: No.

FOLIAGE

Leaf:

*Arrangement*.—Alternate.

*Type*.—Simple.

*Shape of blade*.—Obovate to broad elliptic.

*Average length*.—Approximately 7.0 cm.

*Average width*.—Approximately 4.1 cm.

*Apex*.—Mucronate.

*Base*.—Rounded.

*Attachment*.—Petiolate.

*Margin*.—Entire.

*Texture of top surface*.—Glabrous.

*Texture of bottom surface*.—Glabrous.

*Appearance of top surface*.—Very glossy.

*Appearance of bottom surface*.—Very slightly glossy.

*Leaf internode length*.—Average 2.0 cm.

*Color*.—Young foliage upper side: Main color Yellow 2B, margin Green 137C. Young foliage under side: Main color Yellow 2B, margin Green 137D. Mature foliage upper side: Main color Yellow 2B, margin Green 137A. Mature foliage under side: Main color Yellow 2B, margin Green 137B.

*Venation*.—Type: Pinnate. Venation color upper side: Venation identical to leaf blade color. Venation color under side: Near RHS Green-Yellow 1A.

*Durability of foliage to stresses*.—Flexible and resistant to breakage.

*Fragrance*.—No foliage scent.

Petiole:

*Length*.—Average 1.0 cm.

*Diameter*.—0.3 cm.

*Pubescence*.—None, all surfaces glabrous.

*Color*.—Upper Surface near RHS Greyed-Red 178D. Lower Surface Near RHS Greyed-Red 178D.

FLOWER

Flowering not observed.

OTHER CHARACTERISTICS

Disease and pest resistance: Neither resistance nor susceptibility to normal diseases and pests of *Elaeagnus* has been observed.

Drought tolerance: Established plants have moderate tolerance for drought.

Temperature tolerance: Tolerant to low temperatures of −10° C. High temperature tolerance to about 38° C.

What is claimed is:

1. A new and distinct cultivar of *Elaeagnus* plant named 'Abrela' as herein illustrated and described.

* * * * *